United States Patent [19]
Stephens et al.

[11] Patent Number: 5,454,376
[45] Date of Patent: Oct. 3, 1995

[54] BREATHING MONITOR ARTICLES OF WEARING APPAREL

[76] Inventors: David L. Stephens; David L. Stephens, both of 6221 La Tijera Blvd., Los Angeles, Calif. 90056

[21] Appl. No.: 106,602

[22] Filed: Aug. 16, 1993

[51] Int. Cl.$^6$ ............................................. A61B 5/08
[52] U.S. Cl. ................................ 128/721; 128/644
[58] Field of Search .................... 128/716, 721, 128/644, 671, 722, 725, 782

[56] References Cited

U.S. PATENT DOCUMENTS

| | | | |
|---|---|---|---|
| 3,782,368 | 1/1974 | Reibold | 128/721 |
| 4,296,757 | 10/1981 | Taylor | 128/721 |
| 4,432,368 | 2/1984 | Russek | 128/644 |
| 4,698,848 | 10/1987 | Buckley | 128/644 |
| 4,815,473 | 3/1989 | Watson et al. | 128/721 |
| 4,817,625 | 4/1989 | Miles | 128/721 |
| 4,895,162 | 1/1990 | Dolliver | 128/721 |
| 4,896,307 | 9/1987 | Montgienx | 128/721 |
| 4,909,260 | 3/1990 | Salem et al. | 128/721 |
| 5,191,893 | 3/1993 | Reiten | 128/721 |
| 5,295,490 | 3/1994 | Dodakian | 128/782 |
| 5,301,678 | 4/1994 | Watson et al. | 128/644 |

FOREIGN PATENT DOCUMENTS 2116725  9/1983  United Kingdom ................... 128/721

*Primary Examiner*—Lee S. Cohen
*Assistant Examiner*—Brian M. Green
*Attorney, Agent, or Firm*—Fulwider Patton Lee & Utecht

[57] ABSTRACT

A breathing monitor article of wearing apparel, adapted for child users in order to monitor breathing conditions of a child user. The apparatus and the method of the invention are particularly adaptable for infant child users in order to prevent conditions such as Sudden Infant Death Syndrome and similar conditions arising from apnea. The article of wearing apparel comprises a shirt or like garment adapted to extend around the chest and/or abdomen portion of the child user and which contains a pocket having a monitor therein. An elastic belt extends about the chest and/or abdomen of the user and particularly, in the region of the user's lungs. A strain gauge is secured to the elastic belt and detects breathing movement through the expansion and contraction of the chest wall. The monitor is electronically operated and constructed so as to generate an alarm signal if there is a cessation of breathing for a minimum predetermined time period. The shirt, or like garment, is also constructed so that when it is secured to the child user, it automatically energizes the monitor, thereby eliminating the necessity of an attendant to the child from turning the monitor on or off.

19 Claims, 6 Drawing Sheets

BREATHING MONITOR ARTICLES OF WEARING APPAREL

BACKGROUND OF THE INVENTION

1. Field of the Invention

This invention relates in general to certain new and useful improvements in breathing monitor articles of wearing apparel and more particularly, to an article of wearing apparel which is constructed so as to detect and generate an alarm signal when there is a cessation of breathing of the child user for a minimum predetermined time period.

2. Brief Description of the Prior Art

Detection of breathing patterns of children, and particularly infant children, has proved to be a more difficult task than one would initially envision. There has been a long-felt need for an apparatus and a method to monitor infant child breathing conditions in order to ensure that the child does not lapse into a non-breathing state.

The syndrome of sudden infant death ("SIDS"), is one which is moderately rare, although not uncommon. In the sudden infant death syndrome, oftentimes for some inexplicable reason, the child stops breathing and since there is usually utter silence, a parent, or other attendant to the child, does not recognize the cessation of breathing until long after the death of the infant child. The same situation exists when an infant child becomes entangled in clothing, blankets or the like and is unable to extricate himself or herself. Here, again, suffocation usually occurs, silently resulting in the death of the infant child.

Conditions of periodic cessation of breathing are not uncommon, particularly during the first few days of life. Furthermore, periodic breathing occurs more frequently during periods of active sleep. There has been a need for some apparatus and method to detect improper breathing patterns, particularly when accompanied by reduced heart rate and/or color change. Some of these causes may be due to immature nerve cells, obstructions in the child, chest wall defects or combinations of these causes. In any event, either cessation of breathing or decreased respiratory activity can result either in death or serious or permanent injury to a child, and particularly an infant child.

The control of breathing (often referred to as "ventilation") in infants is determined by the sensitivity of various chemical and physical receptors in the human body to gas and pressures in the body. Sensitivity to oxygen and carbon dioxide in newborn children may be reduced if they do not attain a certain level of grown maturity during gestation and in the first year of their life. Thus, in many cases, these newborn children may experience breathing cessation for ten to fifteen seconds, followed by the condition of apnea for five to ten seconds without a change in skin color or heart rate. As a result, it may be difficult to detect breathing cessation in small children.

Other causes of apnea in infancy include gastroesophageal reflex, pharyngeal incoordination, convulsion, heart disease, infection, CNS abnormality, accidental smothering and breath-holding spells. In each of these cases, external conditions are not immediately apparent and thus, an attendant or parent of the child may not recognize cessation of breathing.

The only effective breathing monitors for infant children are presently located in hospital environments. For example, in one monitor apparatus, a scope is used with leads placed on the child's chest and where the scope is connected to an overhead panel. In this way, an electrical signal, representative of a breathing pattern, may be displayed. A beeper, or other alarm device, may be connected to the scope for audibly generating a signal of heart rate and/or apnea representing an emergency condition. If the frequency on the scope is beyond a certain range which would constitute a normal breathing range, then an alarm will be generated.

One of the problems with this type of equipment is that this equipment obviously is not portable and can only be used by highly trained personnel. Moreover, it is not adapted for home-use environment and is also exceedingly expensive. As a result, this type of equipment is not effective in detecting conditions of apnea, or to reduce the incidence of sudden infant death syndrome in other than a hospital or clinical environment.

In some cases, where an infant child is recognized as having a high risk of sudden breathing cessation, a device which utilizes sonar waves, is attached to the infant's crib and effectively listens for breath sounds. An elastic sheet coupled with an electrode has been used to monitor breathing activity of a child. Unfortunately, this type of device requires a jacket tightly disposed about the chest-wall of the infant child. As a result, it is very uncomfortable and ironically, even militates against the condition it is attempting to monitor in that it actually restricts breathing.

The aforesaid device has also been provided with a shock-type treatment, such that a mild electric shock is applied to the infant child if breathing does not occur for a predetermined period of time. However, this device also has severe drawbacks in that the shock, itself, is distressing to the infant child user and can cause skin burns to the infant child, not to mention the psychological damage which could be created.

There are several infant intercom systems which are commercially available for home use. These intercom systems are generally designed to determine whether a child in another room, or in an environment which is not immediately adjacent to a parent or caretaker, is in a distressed condition, such as crying, etc. However, unless the volume and sensitivity is increased substantially, breathing is not detected. There is also some belief presently that electromagnetic fields produced by these intercom systems can cause brain cancer in infants and others who are in close contact with these systems for prolonged periods of time. Furthermore, when the volume is increased substantially, or if sensitivity is otherwise increased, a hissing noise will result, thereby interfering with a determination of whether or not a breathing pattern is normal. Notwithstanding, after a short time, the breathing pattern becomes background noise and the caretaker or parent is not immediately aware of any lapse in breathing. Even more so, the adult or other caretaker would be required to literally carry a receiver in order to monitor the infant's condition.

OBJECTS OF THE INVENTION

It is, therefore, one of the primary objects of the present invention to provide an article of wearing apparel for use by a child user and which is capable of detecting cessation of breathing in the child user for a minimum predetermined time period.

It is another object of the present invention to provide an article of wearing apparel of the type stated which is capable of generating an alarm signal when breathing cessation occurs for a minimum predetermined time period.

It is a further object of the present invention to provide a child breathing monitor system which involves the use of an article of wearing apparel and which does not inhibit freedom of movement of the child user, or the attendants of the child user.

It is an additional object of the present invention to provide an article of wearing apparel of the type stated which provides for generation of an alarm upon cessation of breathing for a predetermined time period, and which does not require a confined use in a particular environment, such as a hospital or the like.

It is a further object of the present invention to provide an article of wearing apparel capable of detecting breathing cessation of the type stated and which can be constructed at a relatively low cost and which is virtually extremely user friendly in that essentially little or no manual operations are required by an adult in order to enable operation of the article of wearing apparel.

It is another salient object of the present invention to provide a method of monitoring the breathing condition of a child user by merely positioning an article of wearing apparel about a child user.

With the above and other objects in view, my invention resides in the novel features of form, construction, arrangement and combination of parts presently described and pointed out in the claims.

BRIEF SUMMARY OF THE DISCLOSURE

An article of wearing apparel which has the capability of detecting cessation of breathing in a child user for a predetermined minimum time period and which generates an alarm signal if breathing cessation occurs for that minimum time period. In this case, the article of wearing apparel is designed for use about the chest and/or abdomen region of a child, although it is not so limited. Any article which has a portion extending about a portion of the middle or upper torso of the child user can be employed.

The article of wearing apparel, which is capable monitoring breathing conditions, is highly effective for use with infant child users, particularly newborns. However, in many cases, this device can be used with children and adults of many years, and particularly with children and elderly who experience breathing conditions resulting from some physiological disorder. However, and while the apparatus and method of the present invention are not so limited, they are highly effective in enabling the monitoring of any breathing cessation for a period of time which could result in serious injury, if not death, of a child user.

The article of wearing apparel of the present invention comprises a chest-encircling garment to extend around the chest-wall of the child user. A belt is associated with this garment and the belt is not necessarily adapted for use around the waist of the child user. Rather, the belt is adapted for disposition around a portion of the chest-wall of the child user and encircles a portion of that chest-wall.

A gauge means as, for example, a strain gauge, is associated with the belt and is capable of detecting chest-wall expansion and contraction and generating a signal in connection therewith. The article of wearing apparel comprises a monitor which includes a timing means and an alarm signal generating means. The timing means is connected to receive the signals from the gauge means and determines if there is a minimum time period elapse between chest-wall expansion, that is, a lack of breathing for a period which would exceed a minimum predetermined time period. The alarm signal generating means generates an alarm signal if the time period between the chest-wall expansions exceeds this predetermined time limit and thereby enables a monitoring condition.

The article of wearing apparel is more fully characterized in that the chest-encircling garment as, for example, a shirt, extends fully around the upper torso of the child user. Further, the elastic belt should extend fully around, or at least around a substantial portion of the middle or upper torso of the child user.

The shirt, or a similar garment, has a pocket on the external surface which holds a monitor and this monitor includes the timing means and the signal generating means, as aforesaid. Further, one end of this belt preferably extends into and terminates into the pocket on the interior of the shirt. The belt, for this purpose, is preferable an elastic belt. In this way, if the strain gauge, or similar gauge means, is mounted on the surface of the belt, the belt will operate as type of amplifier to amplify the actual chest wall expansion and contraction.

The article of wearing apparel is preferably constructed so that the monitor is located close to the armpit of the child user and is essentially located under the armpit of the child user. In this way, it has been found that the monitor is relatively unobtrusive and does not interfere with normal movement of the child user.

The present invention can also be considered to be an assembly of a type which is used for monitoring the condition of apnea in a child user, but which also relies upon the use of an article of wearing apparel and a monitor associated with that article of wearing apparel. The monitor operates in the manner as previously described and the article of wearing apparel may be any article, as also previously described. The monitor used in this assembly is also effective in that it is programmed to cause generation of a warning signal from the assembly if it is not put in a condition of proper use when disposed on the child user. Furthermore, the monitor is designed to generate a signal indicative of proper disposition on a child user when the article has been properly located on a child user. Finally, a warning signal may be generated if the assembly becomes inoperative while being worn by a child user. In this way, the device of the present invention is quite safe for use.

The present invention also relates to a method for monitoring the conditions of apnea in a child user. This method comprises the disposing of an article of wearing apparel about the upper torso region of a child user. The method further involves the locating of a structural belt with a strain gauge thereon in relation to the article of wearing apparel and also about the upper torso region of the child user. A monitor is positioned on the article of wearing apparel and connected to the strain gauge. An alarm signal is generated if breathing cycles are not detected by the strain gauge within the predetermined time period, in the manner as aforesaid.

The present invention also provides a unique electrical circuit arrangement for operation of an article of wearing apparel which is disposed about a child user, and monitors a condition of apnea in the child user. This electrical circuit arrangement comprises a sensing means for detecting a condition where no breathing has occurred in a minimum predetermined time interval. A processing unit receives the electrical signals from the sensing means in response to breathing activity by a child user. A timing means is provided for generating timing signals to compare against electrical signals from the processing unit. A comparator means compares the electrical signals with timing signals from the timing means to determine if the electrical signals representing breathing activity occurred within this mean minimum predetermined time period. If the comparator means determines that the signals did not occur in the predetermined time period, then an alarm is energized for initiating an audible or visible alarm.

The device of the present invention may be fully adjustable to conform to the size of the child user. It may also be made with fashionable detail and appliques, as desired. Further, all of the electronic components are hidden within a pocket in the shirt and therefore, does not detract from the aesthetic quality which may be built into the article of wearing apparel.

The detection system of the invention has a power-on automatic clearing mechanism. It also is provided with a ready-check monitoring operation. A flash indicator signals a continuous steady state operation so that a user knows that the system is operating properly. The system is effective in counting motion frequency so that an alarm may be triggered if the frequency falls below a certain frequency period.

The monitor of the invention is essentially fail-proof in that excessive pressure on the motion sensor activates a warning indicator. Furthermore, if the belt which holds the gauge should become loosened, a warning signal is also generated. The device is battery operated, but requires very little current in operation. Consequently, the batteries have a relatively long life span when used in the device. The device may also include an internal low power switch and prevent monitor setting and operation and thereby alert the caretaker that batteries may need replacement. The device of the present invention may also be provided with other types of fail-safe alert arrangements.

This invention possesses many other advantages and has other objects and advantages which will become more clearly apparent from a consideration of the forms in which it may be embodied. The following detailed description and the accompanying drawings illustrate a practical embodiment of the invention, although it is to be understood that this detailed description and the accompanying drawings are set forth only for purposes of illustrating the general principles of the invention and are not to be taken in a limiting sense.

BRIEF DESCRIPTION OF THE DRAWINGS

Figure 1:
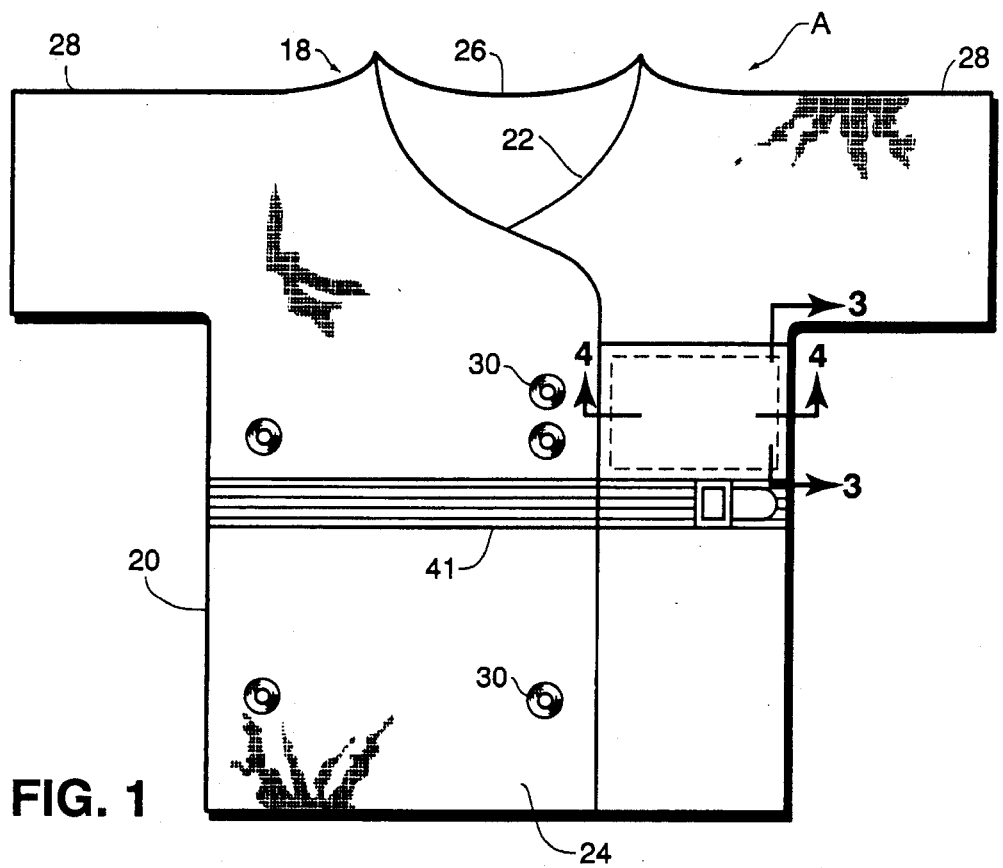
Figure 2:
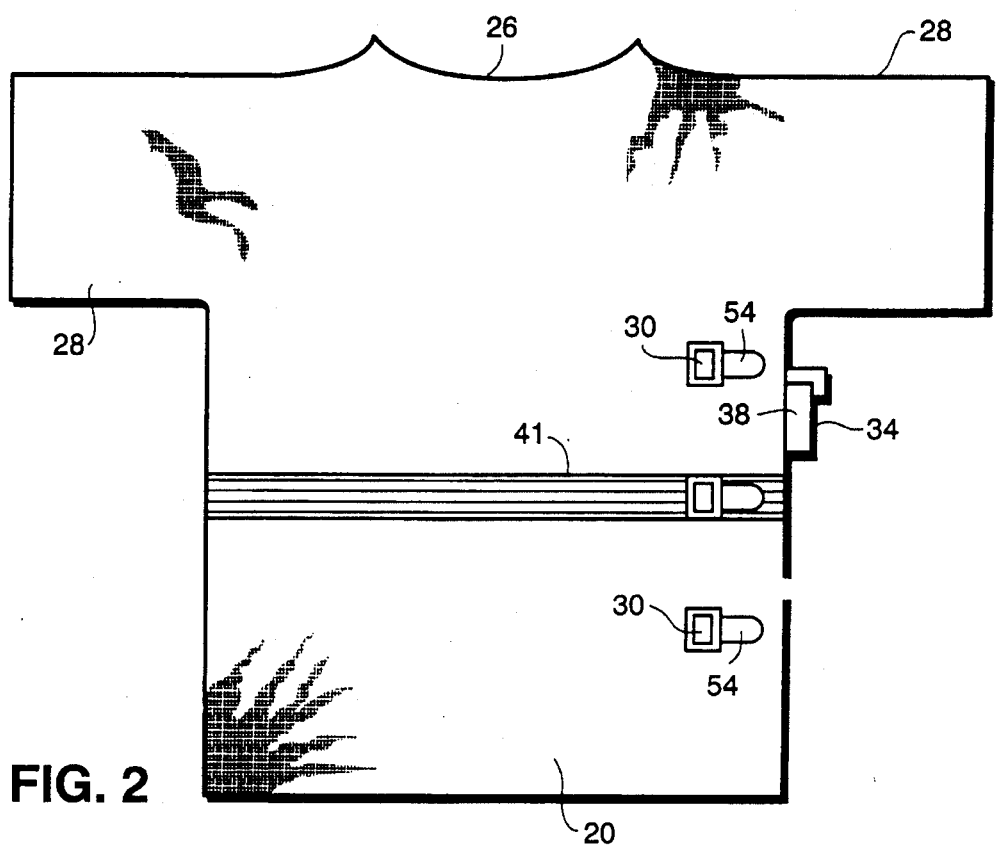
Figure 3:
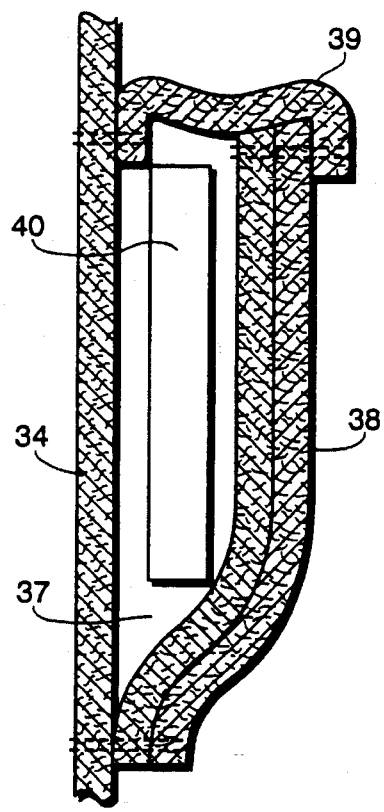
Figure 4:
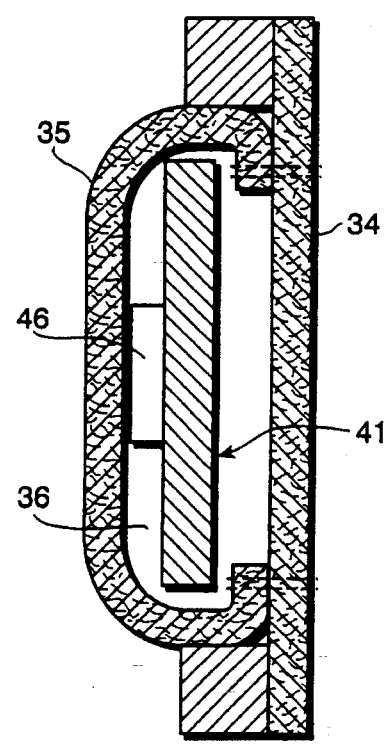
Figure 5:
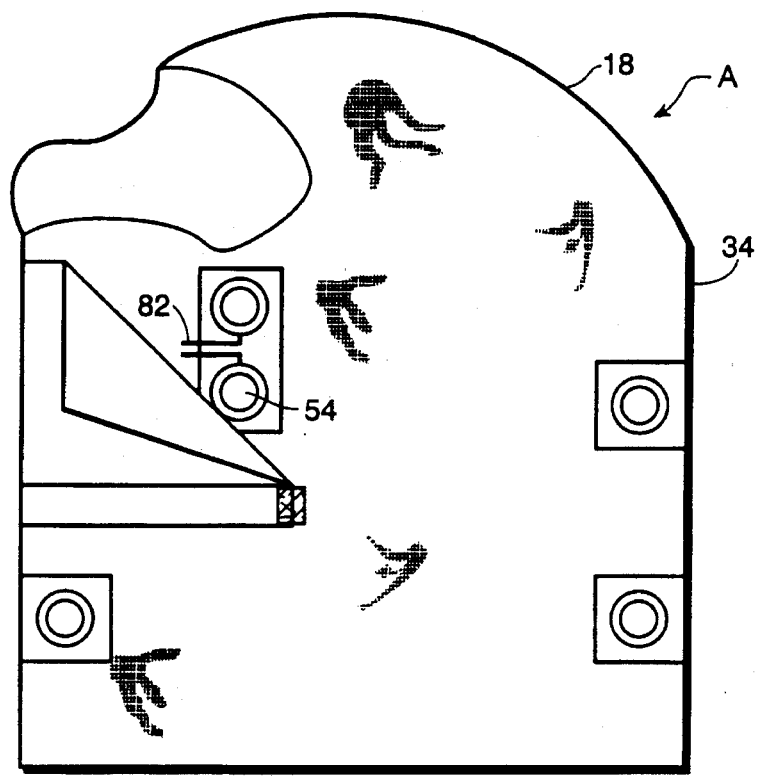
Figure 6:
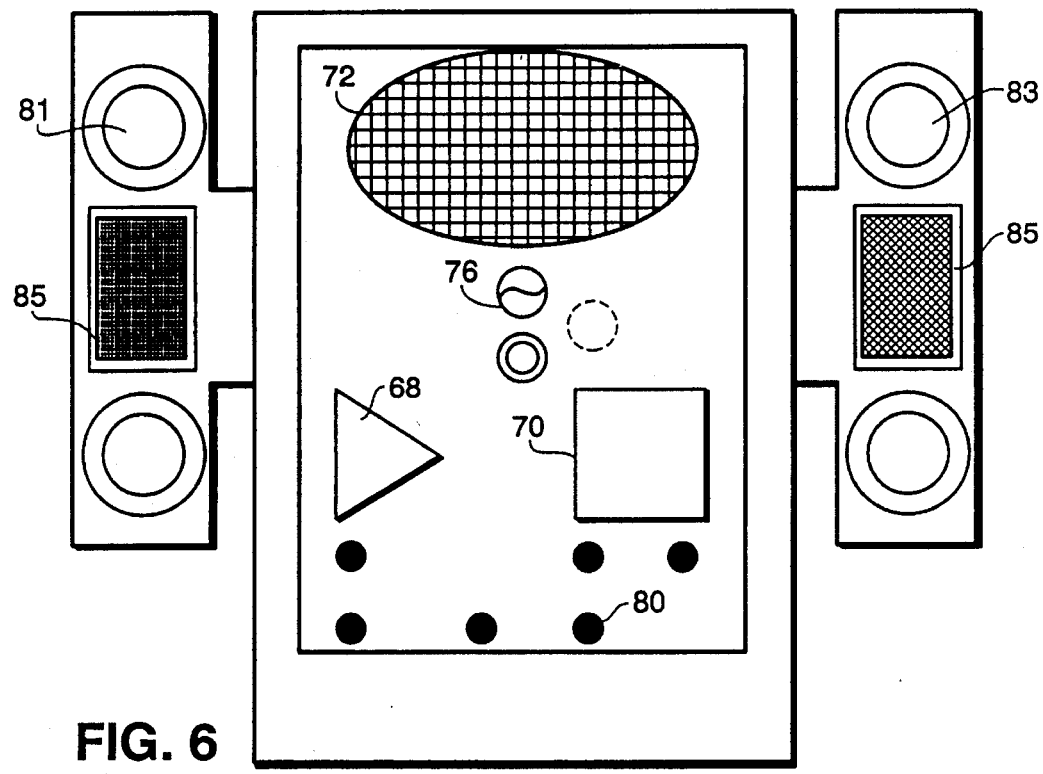
Figure 7:
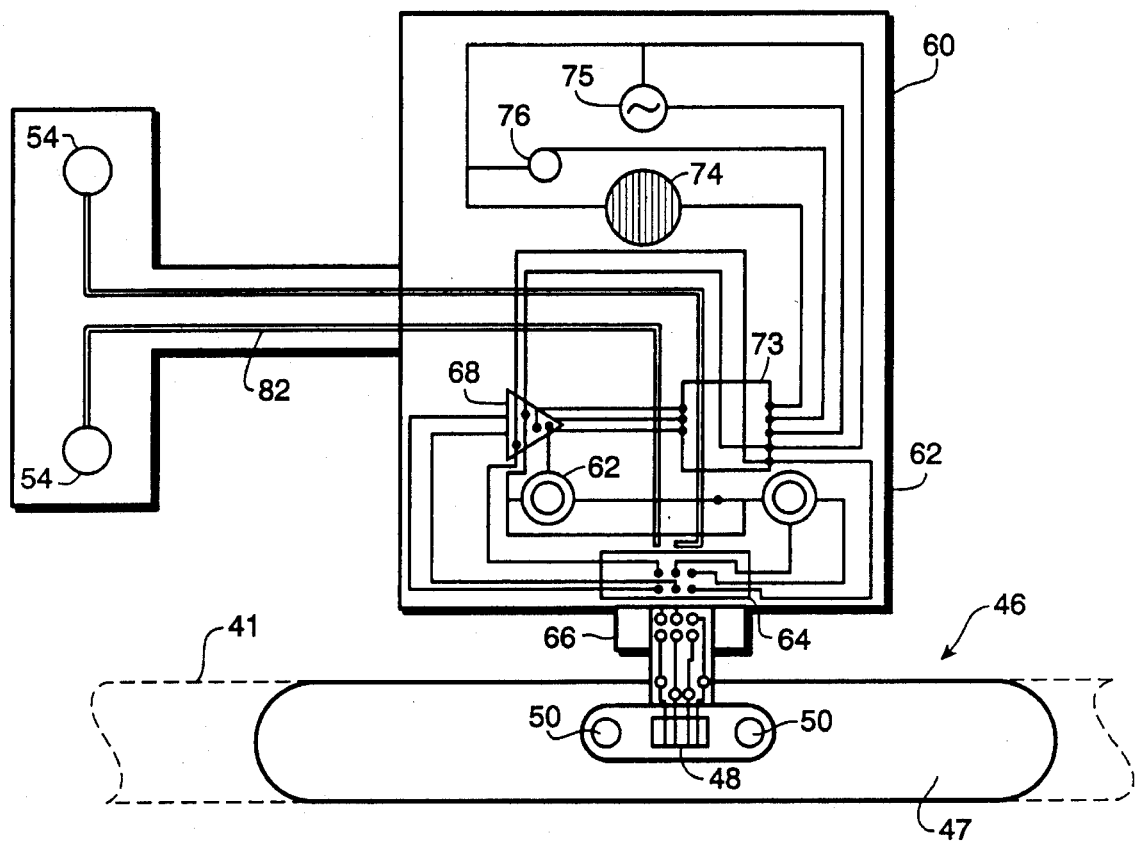

Having thus described the invention in general terms, reference will now be made to the accompanying drawings (six sheets) in which:

FIG. 1 is a front elevational view of a shirt constituting an article of wearing apparel constructed in accordance with and embodying the present invention;

FIG. 2 is an elevational view showing a portion of a slightly modified form of shirt compared to that of FIG. 1;

FIG. 3 is a vertical sectional view taken along line 3—3 of FIG. 1;

FIG. 4 is a horizontal sectional view taken along line 4—4 of FIG. 1;

FIG. 5 is an interior view of the shirt of FIG. 1 showing a portion of an inner pocket folded back to disclose a snap construction used in the device;

FIG. 6 is a plan view of components in the monitor used with the article of wearing apparel of the present invention;

FIG. 7 is somewhat of a schematic plan view showing the arrangement of the components forming part of the monitor and a connection to components on the article of wearing apparel.

Figure 8:
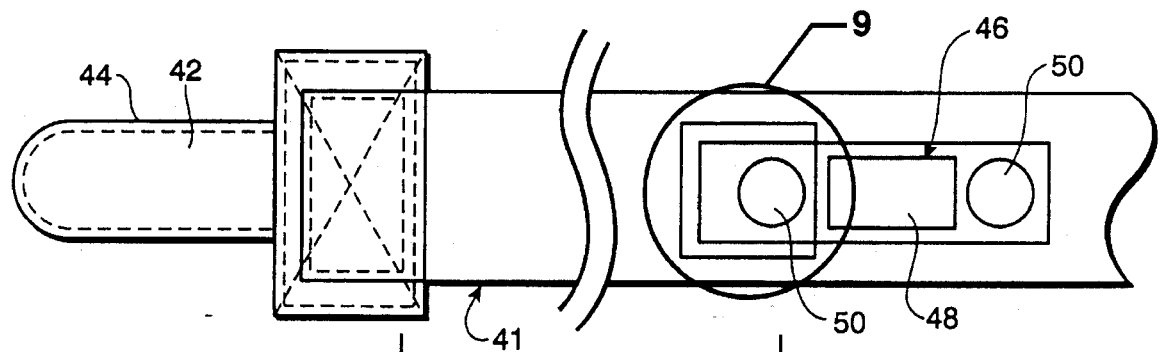
Figure 9:
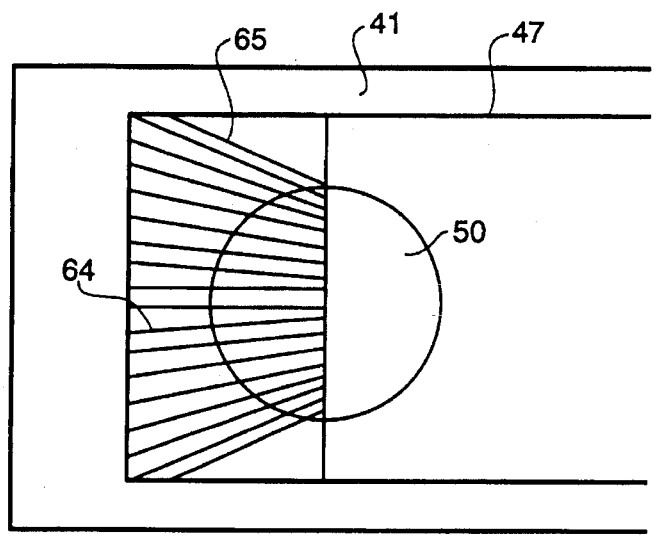
Figure 10:
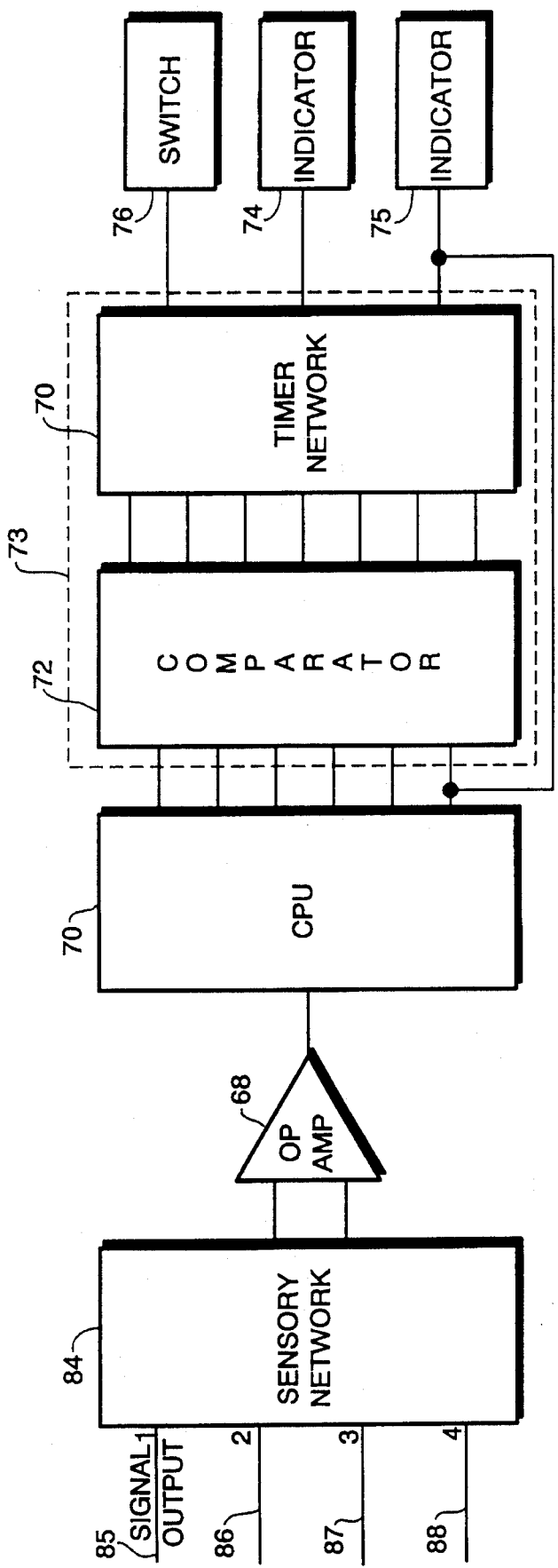
Figure 11:
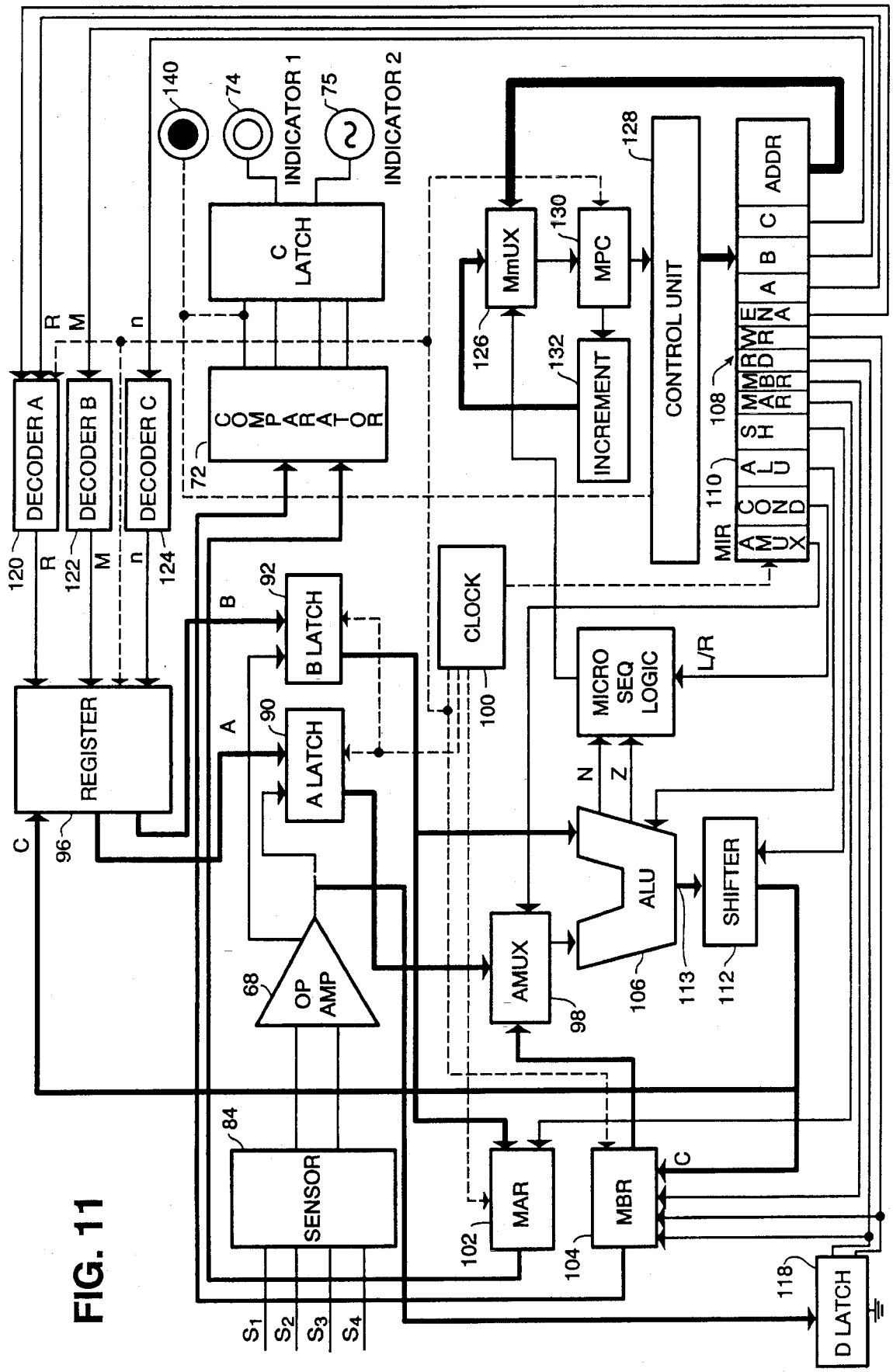

FIG. 8 is an exploded portion of the belt used with the article of wearing apparel;

FIG. 9 is an enlarged detailed view of a portion of the sensor used on the belt of FIG. 8;

FIG. 10 is schematic view showing the major components and a system diagram forming part of the electrical circuity of the present invention; and FIG. 11 is a more detailed circuit schematic view of the circuit forming part of the system of the present invention.

DETAILED DESCRIPTION OF A PREFERRED EMBODIMENT

Referring now in more detail and by reference characters to the drawings which illustrate a preferred embodiment of the invention, A designates an article of wearing apparel in the form of a shirt 18 adapted to be worn about the upper and or middle torso of a child user, and particularly an infant child user. In this case, the shirt comprises a torso-encircling portion 20 terminating in an inner flap 22 and an overlying outer flap 24. The torso-covering portion 20 is provided with an upper neck-receiving region 26 and terminates in a pair of sleeve sections 28, as best shown in FIGS. 1 and 2.

The shirt-like article A may be in the form of a typical undershirt, as shown in FIG. 1. However, it should be understood that this article A can be constructed in a form of a decorative outer shirt arrangement, as shown in FIG. 2, such that it will operate as a monitor and also function as an outer wearing garment. Thus, and in this respect, like reference numerals, as used in FIG. 2, designate similar components in the shirt-like article of FIG. 1. Nevertheless, it should be understood that the illustration of the shirt-like article in FIG. 2 is only representative of a large number of garments which could be used in the present invention.

The shirt-like article A is also provided with a plurality of snap fasteners 30 for securing the overlying outer flap 24 to the inner flap 22, as shown in FIG. 1. However, other forms of releasible fasteners could be provided, although the fasteners must be connected to and cooperate with the monitor as hereinafter described in more detail.

The shirt 18 is formed of a fabric layer 34. Located on the interior portion of the fabric layer 34 is an inner pocket forming closure panel 35, thereby forming an interior pocket 36, as shown in FIGS. 5. Located on the exterior of the shirt A is a monitor-receiving pocket 37 formed by an outer pocket-receiving lining 38 and a closure flap 39. Disposed within the monitor-receiving pocket 37 is a breathing condition monitor 40 which constitutes one of integral portions of the system of the present invention. This monitor 40 is hereinafter described in more detail. The monitor-receiving pocket 37 and the breathing condition monitor 40 is essentially located in a position where it would be close to or under the armpit of the child user. It has been found in connection with the present invention that in this position, the breathing condition monitor 40 presents the least obtrusive appearance and is also the most comfortable position of disposition on the child user.

It is also possible to provide an additional exterior pocket for containing components other than the monitor 40. In this case, a pair of pockets is formed on the shirt itself with the inner pocket effectively being in communication with the exterior pocket. Both the exterior pocket 37 and the interior pocket 36 is of substantially similar construction.

An elastic belt 41 which forms part of the article of wearing apparel is also adapted to extend around an exterior portion of the shirt 18 in the manner as best illustrated in both FIGS. 1 and 2 of the drawings. The elastic belt 41 may be conventionally formed of any elastic material, that is, one capable of stretching and contracting. The elastic belt 41 has an end 42 for manual grasping in order to release and tighten the elastic belt 41. Further, the elastic belt 41 may be provided with fiber-fastening attachment strips, such as the "Velcro strips" 44 on its underside in order to enable releasible attachment. The actual operation of the Velcro, or other fiber-fastening attachment strips, is not illustrated in any detail herein, inasmuch as this is essentially of conventional construction.

Mounted on the elastic belt 41 is a sensor assembly 46, as best illustrated in FIG. 8 of the drawings. By further reference to FIGS. 1 and 2 of the drawings, it can be observed that the elastic belt 41 is worn in a position where it is located essentially immediately beneath the monitor-receiving pocket 37, or at least in the vicinity of the monitor-receiving pocket 37. In either case, the elastic belt 41 is preferably located in the middle or upper torso portion of the child user. In this way, breathing expansion and contraction of a chest of the child user during a breathing cycle will cause an optimum concomitant expansion and retraction of the elastic belt 41. In this way, the elastic belt 41 serves as a type of mechanical force amplifier for the sensor assembly 46.

In a preferred embodiment of the invention the sensor assembly 46 is comprised of a fabric or leather pad 47 with one or more strain gauge sensors 48 mounted thereon, as also best illustrated in FIGS. 8 and 9 of the drawings. Further, any type of sensor which is capable of detecting expansion and contraction of chest movement may be employed for this purpose. The details of mounting the pad 47 are hereinafter described in more detail.

In a preferred embodiment of the invention, the terminal end 42 of the elastic belt can be machine stitched to the shirt itself. In like manner, the shirt may be provided with additional snap 54, as shown in FIG. 5. These additional snap fasteners 54 could, if desired, be located within the monitor-receiving pocket 37.

Located behind the monitor-receiving pocket 37, or within the inner pocket is a snap conductor bus 82 (FIG. 7) which allows current flow to a sensor and monitor arrangement, when snapped or mated with a like fastener. This snap connector bus 82 is more fully hereinafter described in more detail. In any event, when both panels of the shirt are snapped together, and particularly when the elastic belt 41 and monitor 40 is in the electrical circuit, an electrical connection will be created to the breathing condition monitor 40 in accordance with the circuit arrangement, also as hereinafter described in more detail. In like manner, the snap fasteners 30, on the overlying flap 24 are similarly connected to the electrical circuitry forming part of the article of wearing apparel A. By reference to FIG. 2, it can be seen that the snap fasteners 30 can be connected to the similar snap fasteners 54.

The mechanism for fixing the pad 47, containing the strain gauge sensors 48, to the belt 41 is more fully illustrated in FIG. 9 of the drawings. The pad 47 itself is provided with a pair of openings 50, as best illustrated in FIGS. 7 and 9 of the drawings. This pad 47 overlies the material forming the belt 41, as also illustrated in FIG. 9. The openings 50 are used for securing the pad 47, containing the strain gauges 48, to the belt 41 by means of lines of stitching, as illustrated in FIG. 9. In this case, it can be observed that most of the lines of stitching 64 are generally perpendicular to a horizontal center line passing through the openings 50 and particularly with respect to an edge of the openings 50. These lines of stitching 64 are effective to permit a required limited degree of movement of the pad as the belt 41 is stretched. The remaining lines of stitching 65 are somewhat angularly located with respect to the circumference of the opening 50, as also illustrated. This provides a degree of rigidity against complete stretching and also enables the requisite amount of stretching of the pad, if required with the belt. In this way, there is no interference with amplification of the signals to the strain gauges.

Some of the components forming part of the breathing condition monitor 40 are more fully illustrated, at least in schematic form, in FIGS. 6 and 7 of the drawings. In this case, and referring to FIG. 7, it can be seen that the breathing condition monitor 40 comprises an outer housing 60 which includes the electronic components forming part of this breathing condition monitor 40. In particular the breathing condition monitor 40 is operated by a pair of batteries 62, such as conventional disc-type batteries.

The breathing condition monitor 40 is also provided with a socket at one end which is adapted for connection to a mating socket connected to the sensor assembly 46, as also best illustrated in FIGS. 6 and 7 of the drawings. In this way, signals which are generated at the strain gauges 48 will be transmitted to the breathing condition monitor 40 through the bus 82. These signals are amplified by an A6 amplifier 58. The amplified signals from the A6 amplifier 68 are then introduced into a timing circuit which may be a conventional rudimentary type of timer for merely determining whether or not expansion and contraction signals, resulting from chest expansion and contraction, occurred within a predetermined time interval. If the signals generated by the strain gauge 48 did occur within that predetermined time interval, then a condition of normal breathing would be indicated. However, if the signals from the strain gauge 48 did not occur within the predetermined time interval, that would be an indication of an abnormal breathing pattern.

The timing circuit 70 may also include a comparator circuit 72, or may otherwise operate in conjunction with a comparator circuit 72, so as to enable comparison of strain gauge signals with timing signals.

In accordance with the above construction, a fairly simple and inexpensive detection circuit can be employed. If the signals generated at the strain gauge 48 did not occur within a predetermined time period, as established by the timing signals, then an alarm can be generated, as hereinafter described. Any conventional form of the timing circuit 70 may be used for this purpose, as for example, a crystal oscillator or the like.

In a more preferred embodiment, the timing circuit 70 and the comparator circuit 72 form part of a microprocessor 73. Otherwise, the timing circuit 70 can actually be replaced by an integrated circuit processor which would operate with a separate comparator 72 as in a more preferred embodiment of the invention. The integrated circuit microprocessor 73 could be capable of performing not only the timing functions and the comparison function, but to also initiate other signals, as hereinafter described. Thus, and in this respect, the microprocessor 73 would then constitute a so-called "smart" processor.

By reference to both FIGS. 6 and 10, it can be seen that the breathing condition monitor 40 also comprises a conventional buzzer 74 which is connected to the microprocessor 73 and is energized to generate a warning signal if an abnormal breathing pattern is detected. The breathing condition monitor 40 also comprises one or more light-emitting diodes 75 to indicate operation of the apparatus. In this case, a plurality of light-emitting diodes 75 could be employed, so as to indicate the state of the apparatus and any type of condition which might arise. In addition, the breathing condition monitor 40 also comprises a monitor switch 76 which can operate as a type of reset switch. In this way, the user of the apparatus can turn the breathing condition monitor 40 at will by use of the monitor switch 76. In connection with the present invention, it is not necessary to use a manually "on/off" operable monitor switch. For this purpose, the processor 73 could be programmed so as to operate upon connection of the various snap fasteners, as for example, the snap fasteners 30 in mating engagement with the corresponding snap fasteners 54.

FIG. 6 illustrates a schematic type of arrangement of the various components in the breathing condition monitor 40. In this case, it can be observed that the snap or Velcro fasteners 30 are connected to the breathing condition monitor 40, as shown. Furthermore, the breathing condition monitor 40 may be provided with various connector pins 80, as shown in FIG. 6, for electrical connection to various other snap fasteners and the like. Also referring to FIGS. 6 and 7, it can be seen that the various snap or Velcro fasteners 30 are connected to the breathing condition monitor 40 by means of the strap-type conductors 82 which may be mounted within or on the actual fabric material forming part of the shirt 18 or other article of wearing apparel.

The breathing condition monitor itself may be provided with attachment strips which are releasibly attached to the garment itself. For this purpose, fiber-fastening strips of the type offered under the mark Velcro may be employed. Further, snaps may also be employed for securing the breathing condition monitor to the garment itself. FIG. 6 shows the use of a pair of snaps 81 which may be on the monitor itself and cooperate with similar snaps 83 on the shirt. In like manner, Velcro straps 85 may also be employed for this purpose.

FIG. 10 illustrates in electrical schematic form the overall arrangement of the various components forming part of the breathing condition monitor 40. In this case, FIG. 10 illustrates a sensor network 84 which actually comprises the sensory mechanism assembly 46. The sensory network 84 may also comprise other sensors which may form part of the apparatus, as for example, temperature sensors or the like. In the embodiment, as illustrated in FIG. 10, the sensor network 84 receives the positive and negative power inputs 85 and 86 from a battery source of power. In like manner, the sensor network 84 also receives positive and negative strain gauge signals 87 and 88, respectively. The signals from the sensor network 84 are amplified by the operational amplifier 68, as previously described, and then introduced into the microprocessor 73. In this case, the microprocessor 73 comprises the individual comparator 72 and an individual timing network 70, as previously described. The outputs from this circuit include the monitor switch 76, the light emitting diodes 75 and the buzzer 74.

FIG. 11 of the drawings, illustrates in more detail some of the electronic components which form part of the actual circuit arrangement of FIG. 10. As indicated previously, the sensor, comprising at least the network sensor assembly 46, actually receives signals from the strain gauge sensors 48 in sensory-receiving contact with the thoracic wall of the child user and transmits these signals to the operational amplifier 68. The operational amplifier 68 thereupon amplifies the sensed signals and switches the microprocessor 73, sometimes referred to as the central processing unit and which is actually comprised of several of the components in FIG. 11. This begins signal processing by activating an A-latch 90 and a B-latch 92, as well as an arithmetic multiplexer 98.

The central processing unit includes several of the components and may include essentially all of the components of FIG. 11, with the exception of the operational amplifier 68 and the sensor network 84, the indicator lights, e.g. the light-emitting diodes 75, and the buzzer 74, as hereinafter described. In particular, the microprocessor will include a register 96 such as a shift register and which has outputs directed to the A-latch 90 and the B-latch 92. The microprocessor 73 may also be considered to constitute or otherwise include a computer.

The A-latch 90 receives information from the shift register 96, sequentially, and passes this information to the arithmetic multiplexer 98, on command from a main clock generator, or clocking circuit 100. The B-latch 92 also receives information from the shift register 96, and sequentially passes this information to a memory address register 102 on a proper-time basis, in accordance with a signal from the clock generator 100.

The clock generator 100 may be any conventional form of clocking circuit, as, for example, a crystal oscillator-type clock circuit. In this respect, relatively simple components may be used since precise time control in the operation of the various components is not critical.

By further reference to FIG. 11, it can be seen that the arithmetic multiplexer 98 has a pair of data input and one data output. In operation, an N-bit control selects one of the inputs from the A-latch 90 or from a main buffer register 104 and transmits this input to one limb, such as the left-hand limb, of an arithmetic logic unit 106. The arithmetic logic unit 106 receives information from the B-Latch 92, as shown, at its right leg and from a microinstruction register 108 and particularly, an arithmetic logic field 110 of the microinstruction register 108. This, in effect, determines the function of the arithmetic logic unit 106 which is to be performed, such as addition, multiplication, etc. The arithmetic logic unit 106 also has two control inputs which can set the arithmetic logic unit 106 to a positive or a negative state and an input from the microinstruction register 108 which sets the arithmetic logic unit 106 to a zero state.

A shifter 112, which is effectively a 16-bit arithmetic circuit, receives parallel data from the arithmetic logic unit 106 on an input line 113 and which actually constitutes a plurality of individual input lines 113. The shifter 112 will effectively shift one data bit to the right or left, depending upon the signal from an SH field of the microinstruction register 108. Then the data therefrom is transmitted to and stored in the memory buffer register 104.

The memory address register 102 drives the addresses from the B-latch 92 to the comparator 72 for analysis. The memory buffer register 104 drives the data received from the shifter 112 to the comparator 72 and to the arithmetic multiplexer 98.

The circuit includes a C-latch 117 which switches on the appropriate indicator when information from the thoracic wall of the child user and the breathing condition monitoring system 40 is interrupted. In other words, when information at the processing unit (hereinafter described) does not compare with incoming data, the C-latch 117 is initiated.

The circuit further comprises a D-latch 118 which is, in effect, a combination circuit that receives information from the RD and WR fields of the microinstruction register 108, as shown, in order stabilize the operational amplifier 68.

The shift register 96 is a logic circuit which functions as a type of storage unit, as aforesaid. This shift register 96 will enable the recording of a 16-bit word from any of the appropriate decoders, including an A-decoder 120, a B-decoder 122, and a C-decoder 124 at the appropriate time, based on signals from the sensor network 84. At the appropriate subcycle, the shift register 96 will thereupon be clocked to transmit information to the memory address register 102 through the B-latch 92.

Turning again to the main clock circuit 100, this clocking circuit 100 actually functions as a type of computer system drive. The clocking circuit 100 emits periodic sequences of pulses which define the cycles of operation. During each cycle, execution of an instruction from the microinstruction register 108 can occur. The clocking circuit 100 has four outputs, and one of which is a primary output and the other three which are derived from the primary output.

There are several timing subcycles in the operation of the breathing condition monitor 40. In the first subcycle, that is, subcycle 1, information is loaded into the microinstruction register 108 to be executed. In the second subcycle, informtaion stored in register 96 is gated onto the A-latch 90 and the B-latch 92. In the third subcycle, inputs to the circuit are stabilized and transmitted to the arithmetic logic unit 106 and the shifter 112 producing a stable output which may also be loaded into the memory address register 102. In the fourth subcycle, the output of the shifter 112 is stabilized and loaded into the main buffer register 104.

The circuit may include sequential control logic, if desired, having outputs which determine the operation of the microinstruction register 108. This logic may actually form part of and be included within the microinstruction register 108. During the fourth subcycle, as previously described, the arithmetic logic unit 106 output signals are received at the shifter 112. Further, an output from the microinstruction register 108 controls a sequential multiplexer 126 having a primary function to route information and, in this case, to route information to the microprogram controller 130. The latter controller 130 is, in turn, controlled by the ADDR field of the microinstruction register 108. In like manner, the microprocessor control unit 128 causes an information transfer directly to the microinstruction register 108.

To the extent that the components of FIG. 11 are discrete logic components, the circuit could also include a separate microprocessor, counter 130 designated as "MPC" in FIG. 11. The microprocessor counter 130 could, if desired, be incorporated one or more of the other components in FIG. 11.

The microinstruction register 108 is effectively a memory and main control register which enables driving of data to control the other components, as heretofore described. The microinstruction register 108 actually includes thirteen fields which correspond to components of the circuit, or various bus lines. Certain of these fields are hereinafter described.

The microinstruction register 108 includes an AMUX field, which outputs information on a data output bus line of the microinstruction register 108 controls the arithmetic multiplexer 98. A condition field (COND) constitutes a data output of the microinstruction register 108 which determines whether or not the next microinstruction is derived from the MPC+1 field or the ADDR field. An arithmetic logic field (ALU field) constitutes a data output of the microinstruction register 108 which controls the arithmetic logic unit 106. The shift field (SH field) constitutes a data output of the microinstruction register 108 which controls the shifter 112. The main address register field (MAR field) is a data output of the microinstruction register 108 which controls the memory address register 102. In like manner, the main buffer register 104 field (MBR field) is a data output of the microinstruction register 108 which controls the main buffer register 104. The microinstruction register 108 also includes an RD field which constitutes an output controlling the D-latch 118 and the main buffer register 104. A WR field of the microinstruction register 108 also controls the D-latch 118 and the main buffer register 104. An ENA field constitutes a data output of the microinstruction register 108 which controls the A-decoder 120. A C-decoder field (C field) constitutes a data output bus line of the microinstruction register 108 which controls the C-decoder 124. A B-decoder (B field) constitutes an output of the microinstruction register 108 which controls the B-decoder 122. An A-decoder field (A field) constitutes a data output of the microinstruction register 108 which controls the A-decoder 120. An ADDR field of the microinstruction register 108 constitutes an output which sends address messages to the arithmetic multiplexer 130.

The microprocessor counter 130 actually operates in conjunction with the microprocessor control unit 128 to literally control the microinstruction register 108 and the particular function, which is to be next executed. An incrementing circuit 132 is also provided for preparing for the loading of the next sequential instruction and transmits such information to the sequential multiplexer 126. In effect, the microprocessor control unit 128 may also operate as a type of memory for holding the microinstructions for the central processing unit.

The sequential multiplexer 126 is actually a combination circuit that has dual data inputs received from the increment unit 132 and the microinstruction register 108 ADDR field. This increment circuit unit 132 is controlled by the logic circuit which governs the dual input passing through and routes it to the microprocessor control unit 128.

The A-decoder 120 effectively constitutes a combination circuit which has input lines and output lines. The input lines carry information from the microinstruction register 108, and particularly the A field and the ENA field of the microinstruction register 108. If the binary number on the input line is 1, then the output line will be 1, and all other output lines will be 0. The B-decoder 122 is also a circuit which has n input lines and to 2n output lines. The input lines receive information from the MIRB field. If the binary number on the input is 1, then the corresponding output line will be 1 and all other output lines will be 0. The C-decoder 124 is a circuit which also has n input lines and 2n output lines. The input lines receive information from the MIRC field. If the binary number on a particular input line is 1, the number on the corresponding output line will be 1, and all other output lines will be 0.

As indicated previously, the comparator 72 receives information from the memory address register 102 and the main buffer register 104. This comparator 72 compares bits from these registers and when conditions, such as A equal B, A less than B, or A greater than B, do not compare at the appropriate time, C-latch 117 will operate for initiating the actuation of one of the indicator lights or audible alarm.

The circuit also includes a clear switch 140 which operates to reset the clocking circuit, the latches, the registers and the control units to their initial operating state. The buzzer 74 is activated by the C-latch 117 and the lights 74 are also activated by the C-latch 117.

The breathing condition monitor article is quite simple and almost fail-proof in providing automatic monitoring of breathing conditions. Essentially all that is required is to effectively dress the child user. The device is quite reliable and operates on a very low frequency basis. Moreover, it is designed so that it is fairly simple to use, thereby requiring minimal parental or adult education to use.

The device effectively has a built-in motion detecting sensor. The elastic belt 41 may be fully adjustable and may even be provided with a tension check signal, if desired. Furthermore, the electronic conductors are essentially all flat cable and therefore, capable of being easily hidden in the garment and out of the way of the infant user. Moreover, by simple removal of the breathing condition monitor 40, the entire shirt 18 can be washed and dried.

The shirt 18 is constructed so that when the snap fasteners 30 and 54 are initially snapped together, there is an automatic clearing of the components in the monitor. Further, there is a ready check monitoring system. An alert condition signal is generated until a tension signal, representing the connection of the elastic belt 41 is received at the breathing condition monitor 40. The processor of the monitor thereupon initiates a system check and will cause the generation of a signal which may be in the form of an audible signal that identifies to the caretaker that the monitor is correctly operating. This signal may be made by the sound generator, or any of the light-emitting diodes.

The monitoring system operates on a continuous steady-state basis. It is effective for decoding infant motion activity. In effect, the breathing condition monitor 40 counts the motion frequency and is capable of generating a low-motion rate trigger sound generator.

As indicated previously, the entire system is essentially fail-proof. If excess pressure should be applied to the sensor assembly 46, the clear switch forming part of the monitor will activate a warning indicator, such as the buzzer or other sound generator 74. In like manner, a loosened belt will also cause activation of the sound generator 74. Further if the battery power is low, operation is precluded. This type of device which precludes actuation on low battery conditions is known in the art.

The device is also highly effective in that it is comfortable to a child user, such as an infant. Further, it presents little or no possibility of injury to the child. It is essentially 100% reliable in detecting breathing conditions. If the child should happen to lie on the breathing condition monitor 40, this would not interfere with the operation of the apparatus. The breathing condition monitor 40 is provided with a manually operable clear switch such as the monitor switch 76, and this may be pressed to off-set transient spikes. If respiratory motion should cease for about 15 to 30 seconds, the sound generator 74 will be energized and will remain on until the breathing condition monitor 40 is actually reset by the caretaker. Again, if excessive pressure is applied to the breathing condition monitor 40, the sound generator 74 will be activated.

Therefore, it can be seen that the device of the present invention is highly effective and achieves all of the objectives which have been previously described.

Thus, there has been illustrated and described a unique and novel breathing monitor article of wearing apparel which is capable of detecting abnormal breathing conditions and sending out an advisory signal in response thereto. The present invention thereby fulfills all of the objects and advantages which have been sought therefor. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention are deemed to be covered by the invention.

Having thus described the invention, what I desire to claim and secure by Letters Patent is:

1. An article of wearing apparel having the capability of detecting cessation of breathing in a user for a predetermined minimum period of time and generating an alarm signal, said article comprising:

(a) a chest encircling garment adapted to extend around the chest wall of the user, said garment having an interior pocket and an exterior pocket;

(b) a belt associated with said garment and adapted to encircle a portion of the chest wall of the user, said belt extending into said interior pocket and terminating in said interior pocket;

(c) a gauge associated with said belt for detecting chest wall expansion and contraction and generating a signal in response thereto; and (d) timing means connected to receive the signal from said gauge for determining if a time period between chest wall expansions exceeds a predetermined time limit to thereby enable monitoring of the breathing condition of the user, and said exterior pocket of said garment holding a monitor that includes said timing means and an alarm signal generating means for generating the alarm signal when said time period between chest wall expansions exceeds said predetermined time limit.

2. The article of wearing apparel of claim 1 wherein the chest encircling garment is adapted to extend fully around the middle or upper torso of the user, the belt is elastic, and the elastic belt is adapted to extend fully around the middle or upper torso of the user.

3. The article of wearing apparel of claim 1, wherein said belt is an elastic belt and said gauge is mounted on said elastic belt and is located in a region of said interior pocket.

4. The article of wearing apparel of claim 1, wherein said monitor is located on the garment such that it is adapted to be located close to a position where said monitor is almost under the armpit of the user.

5. The article of wearing apparel of claim 1 wherein said gauge is a strain gauge.

6. The article of wearing apparel of claim 1, wherein said belt is an elastic belt and amplifies a chest wall expansion of the user.

7. The article of wearing apparel of claim 1, wherein said chest encircling garment comprises fastening means for securing the article about the chest of the user and said fastening means is connected to said monitor to generate an audible signal that the article is in condition for operation when the fastening means is fastened.

8. An assembly for monitoring conditions of apnea in a child user and particularly an infant child user, said assembly comprising:

(a) a shirt-like article of wearing apparel for wearing engagement by the child user, said shirt-like article including an exterior pocket and an interior pocket;

(b) an elastic belt connected to said article of wearing apparel, said elastic belt being stretchable in response to a chest wall expansion of the child user during a breathing cycle of the child user, said elastic belt extending into said interior pocket;

(c) a strain gauge on said elastic belt and generating an electric signal in response to said chest wall expansion of the child user in a breathing cycle, said strain gauge being disposed in close proximity to said interior pocket; and (d) monitor means connected to said strain gauge for receiving the electrical signal and causing generation of an alarm signal if there is a breathing cessation for a period which could cause injury to the child user, said monitor means being located in said exterior pocket of said shirt-like article.

9. The assembly for monitoring conditions of apnea of claim 8 wherein said monitor means comprises a timing means for determining the occurrence of breathing cycles in a predetermined time period.

10. The assembly for monitoring conditions of apnea of claim 9, wherein an alarm signal generating means for generating the alarm signal is located in said monitor means and is connected to said timing means and causes generation of the alarm signal.

11. The assembly for monitoring conditions of apnea of claim 8 wherein said monitor means causes generation of a warning signal if the assembly is not in a proper condition of use when the article of wearing apparel is first disposed on the child user.

12. The assembly for monitoring conditions of apnea of claim 11 wherein said monitor means generates said warning signal if the assembly should become inoperative while being worn by the child user.

13. An article of wearing apparel having the capability of detecting cessation of breathing in a user for a predetermined minimum period of time and generating an alarm signal, said article comprising:

(a) a chest encircling garment adapted to extend around the chest wall of the user, said garment having a pocket and fastening means for securing the article about the chest of the user and said fastening means is connected to a monitor to generate an audible signal that the article is in condition for operation when the fastening means is fastened;

(b) a belt associated with said garment and adapted to encircle a portion of the chest wall of the user;

(c) a gauge associated with said belt for detecting chest wall expansion and contraction and generating a signal in response thereto; and (d) timing means connected to receive the signal from said gauge for determining if a time period between chest wall expansions exceeds a predetermined time limit to thereby enable monitoring of the breathing condition of the user, and said pocket of said garment holding said monitor that includes said timing means and an alarm signal generating means for generating the alarm signal when said time period between chest wall expansions exceeds said predetermined time limit.

14. The article of wearing apparel of claim 13, wherein the chest encircling garment is adapted to extend fully around the middle or upper torso of the user, the belt is elastic, and the elastic belt is adapted to extend fully around the middle or upper torso of the user.

15. The article of wearing apparel of claim 13, wherein the pocket is an interior pocket and said belt extends into said pocket and terminates in said pocket.

16. The article of wearing apparel of claim 15, wherein said belt is an elastic belt and said gauge is mounted on said elastic belt and is located in a region of said interior pocket.

17. The article of wearing apparel of claim 15, wherein said belt is an elastic belt and amplifies a chest wall expansion of the user.

18. The article of wearing apparel of claim 13, wherein said monitor is located on the garment such that it is adapted to be located close to a position where said monitor is almost under the armpit of the user.

19. The article of wearing apparel of claim 13, wherein said gauge is a strain gauge.

* * * * *